(12) United States Patent
Martin

(10) Patent No.: US 9,565,859 B2
(45) Date of Patent: Feb. 14, 2017

(54) **COMPOSITIONS AND METHODS FOR USE OF INSECTICIDE WITH *BACILLUS* SP. D747**

(71) Applicant: FMC Corporation, Philadelphia, PA (US)

(72) Inventor: Timothy M. Martin, Ringoes, NJ (US)

(73) Assignee: FMC Corporation, Philadelphia, PA (US)

(*) Notice: Subject to any disclaimer, the term of this patent is extended or adjusted under 35 U.S.C. 154(b) by 0 days.

(21) Appl. No.: 14/978,216

(22) Filed: Dec. 22, 2015

(65) Prior Publication Data

US 2016/0183536 A1    Jun. 30, 2016

Related U.S. Application Data

(60) Provisional application No. 62/097,219, filed on Dec. 29, 2014.

(51) Int. Cl.
| | | |
|---|---|---|
| *A01N 63/00* | (2006.01) | |
| *A01N 53/00* | (2006.01) | |
| *C05G 3/02* | (2006.01) | |
| *C05G 3/00* | (2006.01) | |
| *A01N 63/02* | (2006.01) | |

(52) U.S. Cl.
CPC ............... *A01N 63/00* (2013.01); *A01N 53/00* (2013.01); *A01N 63/02* (2013.01); *C05G 3/0064* (2013.01); *C05G 3/02* (2013.01)

(58) Field of Classification Search
None
See application file for complete search history.

(56) References Cited

U.S. PATENT DOCUMENTS

| | | |
|---|---|---|
| 3,060,084 A | 10/1962 | Littler |
| 4,360,376 A | 11/1982 | Koestler |
| 5,583,090 A | 12/1996 | Stern et al. |
| 5,834,006 A | 11/1998 | Smith et al. |
| 5,925,464 A | 7/1999 | Mulqueen et al. |
| 7,094,592 B2 | 8/2006 | Watanabe et al. |
| 8,029,827 B2 | 10/2011 | Martin |
| 8,263,527 B2 | 9/2012 | Martin |
| 8,293,733 B2 | 10/2012 | Giner et al. |
| 8,524,222 B2 | 9/2013 | Jacobsen et al. |
| 8,937,054 B1 | 1/2015 | Martin |
| 8,993,484 B1 | 3/2015 | Martin et al. |
| 2002/0115565 A1 | 8/2002 | Asrar et al. |
| 2004/0023802 A1 | 2/2004 | Asrar et al. |
| 2006/0166898 A1 | 7/2006 | Chen |
| 2007/0135506 A1 | 6/2007 | Zeun et al. |
| 2008/0206361 A1 | 8/2008 | Martin |
| 2008/0306026 A1 | 12/2008 | Shirley et al. |
| 2009/0203746 A1 | 8/2009 | Jadhav et al. |
| 2010/0016392 A1 | 1/2010 | Kabanov et al. |
| 2010/0179198 A1 | 7/2010 | Mertoglu et al. |
| 2010/0234225 A1 | 9/2010 | Dexter et al. |
| 2011/0033436 A1 | 2/2011 | Chen et al. |
| 2011/0053776 A1 | 3/2011 | Bahr |
| 2012/0009238 A1 | 1/2012 | Brahm |
| 2012/0184589 A1 | 7/2012 | Gewehr et al. |
| 2013/0123104 A1 | 5/2013 | McKnight et al. |
| 2013/0236522 A1 | 9/2013 | Misumi |
| 2014/0342914 A1 | 11/2014 | Joost et al. |
| 2015/0099626 A1 | 4/2015 | Martin |
| 2015/0099627 A1 | 4/2015 | Martin et al. |
| 2015/0099628 A1 | 4/2015 | Martin et al. |

FOREIGN PATENT DOCUMENTS

| | | |
|---|---|---|
| EP | 2716748 A1 | 4/2014 |
| WO | 01/26468 A2 | 4/2001 |
| WO | 2009/049747 A2 | 4/2009 |
| WO | 2009/091557 A1 | 7/2009 |
| WO | 2009/124707 A2 | 10/2009 |

OTHER PUBLICATIONS

International Search Report issued Nov. 5, 2014 in International Application No. PCT/US14/58569 to FMC Corporation (9 pages).
Merriam Webster Online dictionary, obtained online at: http://www.merriam-webster.com/dictionary/fertilizer, downloaded on Sep. 11, 2014.
International Search Report issued Oct. 21, 2014 in International Patent Application No. PCT/US14/58515 to FMC Corporation (11 pages).
International Search Report issued Oct. 23, 2014 in International Patent Appln. No. PCT/US14/58521 to FMC Corporation (10 pages).
International Search Report issued Oct. 23, 2014 in International Patent Application No. PCT/US14/58591 to FMC Corporation (11 pages).
International Search Report and Written Opinion mailed Jan. 4, 2016 in International Patent Application No. PCT/US2015/053104 (8 pages).
Database WPI, Week 201126, XP0002752081, Thomson Scientific, Dec. 15, 2010.
Database WPI, Week 201082, XP-002752082, Thomson Scientific, Oct. 6, 2010.
International Search Report and Written Opinion mailed Feb. 13, 2015 in International Patent Application No. PCT/US2014/068571.
Ashland Safety Data Sheet for DEXTROL™ OC-180 dated May 21, 2015 (13 pages).
Safety Data Sheet for REXA® 88B dated Feb. 10, 2015 (15 pages).
Safety Data Sheet for "SOKOLAN CP9" dated Apr. 29, 2015 (9 pages).
Product label for AMMO 2.5 EC Insecticide (Cypermethrin)dated Jul. 31, 2012 (5 pages).
Safety Data Sheet for Attaflow® FL (Attapulgite Clay) dated Aug. 7, 2014 (10 pages).
Product label for BRIGADE® 2EC Insecticide/Miticide (Bifenthrin) dated Oct. 2, 2012 (25 pages).
Product label for GLADIATOR™ insecticide/miticide (Zeta-Cypermethrin/Avermectin) dated Jul. 9, 2012 (23 pages).

(Continued)

*Primary Examiner* — Alton Pryor
(74) *Attorney, Agent, or Firm* — Fox Rothschild LLP

(57) ABSTRACT

Compositions and methods are provided for benefiting plant growth. In particular aspects, the compositions contain a biologically pure culture of *Bacillus* sp. D747 strain (deposited as FERM BP-8234) and an insecticide in a formulation suitable for dissolution in a liquid fertilizer.

30 Claims, No Drawings

(56) References Cited

OTHER PUBLICATIONS

Material Safety Data Sheet for Myconate HB (Formononetin) dated Sep. 8, 2009 (4 pages).
Product label for NUFOS® 4E insecticide (Chlorpyrifos) dated Dec. 20, 2012 (39 pages).
Extended label for RATCHET™ liquid dated Aug. 2011 (2 pages).
Safety Data Sheet for SOKALAN® CP 10 dated Mar. 9, 2015 (9 pages).
Product Label for TALSTAR PL Granular insecticide dated Mar. 21, 2011 (3 pages).
Product Label for ZORO® Miticide/Insecticide (Abamectin) dated Mar. 29, 2012 (31 pages).
Third Party Observation submitted Mar. 30, 2016 relating to International Application No. PCT/US2014/068571 (5 pages).
Product Label for CAPTURE® LFR™ insecticide (Bifenthrin) dated Apr. 4, 2013 (19 pages).
International Search Report and Written Opinion mailed Mar. 7, 2016 in International Patent Application No. PCT/US2015/067353.
Biopesticides Registration Action Document. Dec. 8, 2011.
Kloepper, Joseph W. et al., Induced Systemic Resistance and Promotion of Plant Growth by *Bacillus* spp., Pytopathology, vol. 94, No. 11, 2004, 1259-1266.
Bergey's Manual of Systematic Bacteriology, vol. 1 (1984)— (Voluminous).

COMPOSITIONS AND METHODS FOR USE OF INSECTICIDE WITH *BACILLUS* SP. D747

CROSS-REFERENCE TO RELATED APPLICATION

This application claims the benefit of U.S. Provisional Application No. 62/097,219 filed Dec. 29, 2014, the disclosure of which is incorporated herein by reference in its entirety.

FIELD OF THE INVENTION

The present invention relates to the field of agricultural compositions and formulations. In particular, aspects of the presently disclosed subject matter relate to an insecticidal composition in combination with a biological control agent. In certain aspects, the composition is useful in the preparation of insecticidal liquid fertilizers.

BACKGROUND OF THE INVENTION

To enable the efficient elimination or control of unwanted insects in combination with providing nutrients for plants to combat adverse environmental conditions (such as heat, drought, physical contact with animals, etc.) it is desirable to formulate an effective chemical insecticide for use in preparation of insecticidal liquid fertilizers. Formulations of insecticides combined with fertilizers are desirable in agricultural and related endeavors due to the multiple benefits conveyed by just one application in a single piece of equipment. One application of such a combination or formulation provides nutrients for the plant growth, while eliminating or controlling unwanted insects that can also affect the health and vitality of the desirable plants.

Mixtures containing insecticide compositions and liquid fertilizers have been practiced in the art, but problems with the physical stability of such mixtures have caused application and efficacy issues. When a traditional insecticidal composition is combined with a liquid fertilizer, the combined components (surfactants, viscosity modifiers, wetting agents) of both can cause accelerated physical degradation (phase separation) of the mixture. This physical degradation can occur in the mix tanks prior to application on the plants. Often this problem goes unnoticed and results in inconsistent application of both the fertilizer and insecticide, yielding inadequate efficacy of both.

The use of a microorganism (which may be termed a biological control agent) in a composition suitable for use in the preparation of insecticidal liquid fertilizer may provide additional efficacy.

A number of microorganisms having beneficial effects on plant growth and health are known to be present in the soil, to live in association with plants specifically in the root zone (Plant Growth Promoting Rhizobacteria "PGPR"), or to reside as endophytes within the plant. Their beneficial plant growth promoting properties include nitrogen fixation, iron chelation, phosphate solubilization, inhibition of non-beneficial microorganisms, resistance to pests, Induced Systemic Resistance (ISR), Systemic Acquired Resistance (SAR), decomposition of plant material in soil to increase useful soil organic matter, and synthesis of phytohormones such as indole-acetic acid (IAA), acetoin and 2,3-butanediol that stimulate plant growth, development and responses to environmental stresses such as drought. In addition, these microorganisms can interfere with a plant's ethylene stress response by breaking down the precursor molecule, 1-aminocyclopropane-1-carboxylate (ACC), and thereby stimulating plant growth and slowing fruit ripening. These beneficial microorganisms can improve soil quality, plant growth, yield, and quality of crops. Various microorganisms exhibit biological activity such as to be useful to control plant diseases. Such biopesticides (living organisms and the compounds naturally produced by these organisms) can be safer and more biodegradable than synthetic fertilizers and pesticides.

Fungal phytopathogens, including but not limited to *Botrytis* spp. (e.g. *Botrytis cinerea*), *Fusarium* spp. (e.g. *F. oxysporum* and *F. graminearum*), *Rhizoctonia* spp. (e.g. *R. solani*), *Magnaporthe* spp., *Mycosphaerella* spp., *Puccinia* spp. (e.g. *P. recondita*), *Phytopthora* spp. and *Phakopsora* spp. (e.g. *P. pachyrhizi*), are one type of plant pest that can cause severe economic losses in the agricultural and horticultural industries. Chemical agents can be used to control fungal phytopathogens, but the use of chemical agents suffers from disadvantages including high cost, lack of efficacy, emergence of resistant strains of the fungi, and undesirable environmental impacts. In addition, such chemical treatments tend to be indiscriminant and may adversely affect beneficial bacteria, fungi, and arthropods in addition to the plant pathogen at which the treatments are targeted. A second type of plant pest are bacterial pathogens, including but not limited to *Erwinia* spp. (such as *Erwinia chrysanthemi*), *Pantoea* spp. (such as *P. citrea*), *Xanthomonas* (e.g. *Xanthomonas campestris*), *Pseudomonas* spp. (such as *P. syringae*) and *Ralstonia* spp. (such as *R. soleacearum*) that cause severe economic losses in the agricultural and horticultural industries. Similar to pathogenic fungi, the use of chemical agents to treat these bacterial pathogens suffers from disadvantages. Viruses and virus-like organisms comprise a third type of plant disease-causing agent that is hard to control, but to which bacterial microorganisms can provide resistance in plants via induced systemic resistance (ISR). Thus, microorganisms that can be applied as biofertilizer and/or biopesticide to control pathogenic fungi, viruses, and bacteria are desirable and in high demand to improve agricultural sustainability. A final type of plant pathogen includes plant pathogenic nematodes and insects, which can cause severe damage and loss of plants.

Some members of the species *Bacillus* have been reported as biocontrol strains, and some have been applied in commercial products (Joseph W. Kloepper et al., *Phytopathology* Vol. 94, No. 11, 2004 1259-1266). For example, strains currently being used in commercial biocontrol products include: *Bacillus pumilus* strain QST2808, used as active ingredient in SONATA and BALLAD-PLUS, produced by BAYER CROP SCIENCE; *Bacillus pumilus* strain GB34, used as active ingredient in YIELDSHIELD, produced by BAYER CROP SCIENCE; *Bacillus subtilis* strain QST713, used as the active ingredient of SERENADE, produced by BAYER CROP SCIENCE; *Bacillus subtilis* strain GBO3, used as the active ingredient in KODIAK and SYSTEM3, produced by HELENA CHEMICAL COMPANY. Various strains of *Bacillus thuringiensis* and *Bacillus firmus* have been applied as biocontrol agents against nematodes and vector insects and these strains serve as the basis of numerous commercially available biocontrol products, including NORTICA and PONCHO-VOTIVO, produced by BAYER CROP SCIENCE. In addition, *Bacillus* strains currently being used in commercial biostimulant products include: *Bacillus amyloliquefaciens* strain FZB42 used as the active ingredient in RHIZOVITAL 42, produced by ABiTEP GmbH, as well as various other *Bacillus subtilis* species that are included as whole cells including their fermentation extracts in biostimulant products, such as FULZYME produced by JHBiotech Inc.

Bacillus sp. D747 strain has been described as a biological control agent useful for controlling a number of plant diseases, including, but not limited to, fungal diseases. U.S. Pat. No. 7,094,592 to Watanabe et al., incorporated herein by reference in its entirety, describes the biological characteristics of the Bacillus sp. D747 strain, including bacteriological characteristics in accordance with Bergey's Manual of Systematic Bacteriology, Volume 1 (1984). U.S. Patent Publication No. 2013/0236522 to Misumi describes use of Bacillus sp. D747 strain in formulations such as a dust, granule or powder.

The Bacillus sp. D747 strain was deposited at the National Institute of Advanced Industrial Science and Technology, International Patent Organism Depositary as "Bacillus sp. D747" with Accession Number "FERM P-18128", and was then transferred to be deposited under the Budapest Treaty on Nov. 8, 2002, as "Bacillus sp. D747" with new Accession Number "FERM BP-8234".

SUMMARY OF THE INVENTION

In one embodiment of the present invention a composition is provided for benefiting plant growth, the composition comprising: a biologically pure culture of Bacillus sp. D747 strain having properties beneficial to plant growth and one or more microbial or chemical pesticide, in a formulation compatible with a liquid fertilizer, wherein the bacterial strain and the one or more microbial or chemical pesticide are present in an amount suitable to benefit plant growth.

In one embodiment of the present invention a composition is provided for benefiting plant growth, the composition comprising: a biologically pure culture of Bacillus sp. D747 strain deposited as FERM BP-8234, and an insecticide in a formulation compatible with a liquid fertilizer, wherein each of the Bacillus sp. D747 strain deposited as FERM BP-8234 and the insecticide is present in an amount suitable to benefit plant growth.

In one embodiment of the present invention a product is provided, the product comprising: a first composition comprising a biologically pure culture of Bacillus sp. D747 strain deposited as FERM BP-8234; a second composition comprising an insecticide in a formulation compatible with a liquid fertilizer, wherein the first and second compositions are separately packaged, and wherein each component is in an amount suitable to benefit plant growth; and optionally instructions for delivering in a liquid fertilizer and in an amount suitable to benefit plant growth, a combination of the first and second compositions to one or more of: seed of the plant, roots of the plant, a cutting of the plant, a graft of the plant, callus tissue of the plant; soil or growth medium surrounding the plant; soil or growth medium before sowing seed of the plant in the soil or growth medium; or soil or growth medium before planting the plant, the plant cutting, the plant graft, or the plant callus tissue in the soil or growth medium.

In one embodiment of the present invention a method is provided for benefiting plant growth, the method comprising: delivering to a plant in a liquid fertilizer composition, wherein the composition comprises: a biologically pure culture of Bacillus sp. D747 strain deposited as FERM BP-8234 and an insecticide in a formulation compatible with a liquid fertilizer, wherein each of the Bacillus sp. D747 strain and the insecticide is present in an amount sufficient to benefit plant growth, wherein the composition is delivered in the liquid fertilizer in an amount suitable for benefiting plant growth to one or more of: seed of the plant, roots of the plant, a cutting of the plant, a graft of the plant, callus tissue of the plant, soil or growth medium surrounding the plant, soil or growth medium before sowing seed of the plant in the soil or growth medium, or soil or growth medium before planting the plant, the plant cutting, the plant graft, or the plant callus tissue in the soil or growth medium.

In one embodiment of the present invention a method is provided for benefiting plant growth, the method comprising: delivering in a liquid fertilizer in an amount suitable for benefiting plant growth a combination of: a first composition having a biologically pure culture of Bacillus sp. D747 strain deposited as FERM BP-8234; and a second composition having an insecticide, wherein each composition is in a formulation compatible with a liquid fertilizer and wherein each component is in an amount suitable to benefit plant growth, and wherein the combination is delivered to one or more of: seed of the plant, roots of the plant, a cutting of the plant, a graft of the plant, callus tissue of the plant; soil or growth medium surrounding the plant; soil or growth medium before sowing seed of the plant in the soil or growth medium; or soil or growth medium before planting the plant, the plant cutting, the plant graft, or the plant callus tissue in the soil or growth medium.

In other embodiments of the present invention, a composition is provided comprising a biologically pure culture of Bacillus sp. D747 strain deposited as FERM BP-8234; and a bifenthrin insecticide composition. In one embodiment, the bifenthrin composition may comprise: bifenthrin; a hydrated aluminum-magnesium silicate; and at least one dispersant selected from a sucrose ester, a lignosulfonate, an alkylpolyglycoside, a naphthalenesulfonic acid formaldehyde condensate and a phosphate ester. In an embodiment, the composition may be an aqueous based formulation.

In some embodiments, the hydrated aluminum-magnesium silicate is selected from the group consisting of montmorillonite and attapulgite. In some embodiments, the phosphate ester is selected from a nonyl phenol phosphate ester and a tridecyl alcohol ethoxylated phosphate potassium salt. Some embodiments further include a liquid fertilizer. Other embodiments further include at least one of an anti-freeze agent, an anti-foam agent and a biocide.

Some embodiments provide a method of making a composition, the method comprising dispersing bifenthrin in a mixture of water and at least one dispersant; and optionally, an anti-freeze agent, an anti-foam agent and/or a biocide; wet milling the mixture, adding a hydrated aluminum-magnesium silicate and blending the mixture. To the mixture is added a biologically pure culture of Bacillus sp. D747. In some embodiments, the process may further comprise adding the resultant mixture to a liquid fertilizer.

DETAILED DESCRIPTION OF THE INVENTION

The terms "a," "an," and "the" refer to "one or more" when used in this application, including the claims. Thus, for example, reference to "a plant" includes a plurality of plants, unless the context clearly is to the contrary, and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Compositions and methods are provided for benefiting plant growth. In some embodiments, the compositions may contain isolated bacterial strains having properties beneficial to plant growth and development that can provide beneficial growth effects when delivered in a liquid fertilizer to plants, seeds, or the soil or other growth medium surrounding the plant or seed in combination with a soil insecticide.

As used in this specification and unless otherwise indicated the term "insecticide" refers to a molecule or combination of molecules that repels, retards, or kills insects, and can be used for crop protection, edifice protection, turf protection, or protection of a person.

The phrases "plant growth promoting" and "plant growth benefit" and "benefiting plant growth" and "properties beneficial to plant growth" and "properties beneficial to plant growth and development" are intended to mean and to be exhibited by for purposes of the specification and claims one or a combination of: improved seedling vigor, improved root development, improved plant health, increased plant mass, increased yield, improved appearance, or improved resistance to plant pathogens.

As is employed herein, the term "plant growth effective amount" refers to an amount of a composition which will increase the growth and or vigor of the plant as described herein to an extent exceeding that of identical plants not treated with the composition.

As is employed herein, the term "plants" includes agricultural, silvicultural and horticultural (including ornamental) plants. The term "plants" also includes genetically modified plants in which genetic material has been modified by the use of recombinant DNA techniques.

Such techniques permit modifications that cannot readily be obtained by natural breeding or mutagenesis, such as, for example, cross-breeding under natural circumstances, natural mutations or natural recombination.

In particular, for example, the plant may include, but is not limited to, food crops, monocots, dicots, fiber crops, cotton, biofuel crops, cereals, Corn, Sweet Corn, Popcorn, Seed Corn, Silage Corn, Field Corn, Rice, Wheat, Barley, Sorghum, *Brassica* Vegetables, Broccoli, Cabbage, Cauliflower, Brussels Sprouts, Collards, Kale, Mustard Greens, Kohlrabi, Bulb Vegetables, Onion, Garlic, Shallots, Fruiting Vegetables, Pepper, Tomato, Eggplant, Ground Cherry, Tomatillo, Okra, Grape, Herbs/Spices, Cucurbit Vegetables, Cucumber, Cantaloupe, Melon, Muskmelon, Squash, Watermelon, Pumpkin, Eggplant, Leafy Vegetables, Lettuce, Celery, Spinach, Parsley, Radicchio, Legumes/Vegetables (succulent and dried beans and peas), Beans, Green beans, Snap beans, Shell beans, Soybeans, Dry Beans, Garbanzo beans, Lima beans, Peas, Chick peas, Split peas, Lentils, Oil Seed Crops, Canola, Castor, Cotton, Flax, Peanut, Rapeseed, Safflower, Sesame, Sunflower, Soybean, Root/Tuber and Corm Vegetables, Carrot, Potato, Sweet Potato, Beets, Ginger, Horseradish, Radish, *Ginseng*, Turnip, sugarcane, sugarbeet, Grass, or Turf grass.

The term "liquid fertilizer" refers to a fertilizer in a fluid or liquid form containing various ratios of nitrogen, phosphorous and potassium (for example, but not limited to, 10% nitrogen, 34% phosphorous and 0% potassium) and micronutrients, commonly known as starter fertilizers that are high in phosphorus and promote rapid and vigorous root growth.

As used herein, the phrase "a biologically pure culture of a bacterial strain" refers to one or a combination of: spores of the biologically pure fermentation culture of a bacterial strain, vegetative cells of the biologically pure fermentation culture of a bacterial strain, one or more products of the biologically pure fermentation culture of a bacterial strain, a culture solid of the biologically pure fermentation culture of a bacterial strain, a culture supernatant of the biologically pure fermentation culture of a bacterial strain, an extract of the biologically pure fermentation culture of the bacterial strain, and one or more metabolites of the biologically pure fermentation culture of a bacterial strain.

The compositions can be delivered to plant material including, but not limited to, a seed of the plant, roots of the plant, a cutting of the plant, a graft of the plant, callus tissue of the plant, soil or growth medium surrounding the plant, soil or growth medium before sowing seed of the plant in the soil or growth medium, or soil or growth medium before planting the plant, the plant cutting, the plant graft, or the plant callus tissue in the soil or growth medium.

In one embodiment, a composition is provided for benefiting plant growth, the composition having a biologically pure culture of a bacterial strain having properties beneficial to plant growth and a soil insecticide in a formulation compatible with a liquid fertilizer, wherein each of the bacterial strains and the soil insecticide is present in an amount suitable to benefit plant growth. In embodiments, the composition may be in the form of a liquid. The bacterial strain can be in the form of spores or vegetative cells. The bacterial strain can be a strain of *Bacillus*. The *Bacillus* can be a biologically pure culture of *Bacillus* sp. D747 strain deposited as FERM BP-8234.

The terms "in a formulation suitable as a liquid fertilizer" and "in a formulation compatible with a liquid fertilizer" are herein used interchangeably throughout the specification and claims and are intended to mean that the formulation is capable of dissolution or dispersion or emulsion in an aqueous solution to allow for mixing with a fertilizer for delivery to plants in a liquid formulation.

In another embodiment, a product is provided for benefiting plant growth, the product including a first component comprising a first composition comprising a biologically pure culture of a bacterial strain having properties beneficial to plant growth and a second component comprising a second composition comprising a soil insecticide. In this embodiment, the first and second components can be separately packaged and each component is in a formulation compatible with a liquid fertilizer. Each component is in an amount suitable to benefit plant growth. Instructions can be provided for delivering in a liquid fertilizer and in an amount suitable to benefit plant growth, a combination of the first and second compositions to one or more of: seed of the plant, roots of the plant, a cutting of the plant, a graft of the plant, callus tissue of the plant; soil or growth medium surrounding the plant; soil or growth medium before sowing seed of the plant in the soil or growth medium; or soil or growth medium before planting the plant, the plant cutting, the plant graft, or the plant callus tissue in the soil or growth medium. The bacterial strain can be in the form of spores or vegetative cells. The bacterial strain can be a strain of

*Bacillus.* The *Bacillus* may be a biologically pure culture of *Bacillus* sp. D747 strain deposited as FERM BP-8234.

In one embodiment, a method is provided for benefiting plant growth that comprises delivering to a plant in a liquid fertilizer a composition comprising a biologically pure culture of a bacterial strain having properties beneficial to plant growth and a soil insecticide in a formulation compatible with a liquid fertilizer. Each of the bacterial strains and the soil insecticide is present in an amount sufficient to benefit plant growth. The composition can be delivered in the liquid fertilizer in an amount suitable for benefiting plant growth to one or more of: seed of the plant, roots of the plant, a cutting of the plant, a graft of the plant, callus tissue of the plant, soil or growth medium surrounding the plant, soil or growth medium before sowing seed of the plant in the soil or growth medium, or soil or growth medium before planting the plant, the plant cutting, the plant graft, or the plant callus tissue in the soil or growth medium.

In another embodiment, a method is provided for benefiting plant growth that comprises delivering in a liquid fertilizer in an amount suitable for benefiting plant growth a combination of a first composition comprising a biologically pure culture of a bacterial strain having properties beneficial to plant growth and a second composition comprising a soil insecticide. Each component is in a formulation compatible with a liquid fertilizer and each component is in an amount suitable to benefit plant growth. The composition can be delivered to one or more of: seed of the plant, roots of the plant, a cutting of the plant, a graft of the plant, callus tissue of the plant; soil or growth medium surrounding the plant, soil or growth medium before sowing seed of the plant in the soil or growth medium, or soil or growth medium before planting the plant, the plant cutting, the plant graft, or the plant callus tissue in the soil or growth medium.

The isolated bacterial strain of the present invention can be a strain of *Bacillus*. The *Bacillus* may be a biologically pure culture of *Bacillus* sp. D747 strain deposited as FERM BP-8234.

The bacterial strain can be in the form of spores or vegetative cells. The amount of the bacterial strain suitable for benefiting plant growth can range from about $1.0 \times 10$ CFU/ha to about $1.0 \times 10^{13}$ CFU/ha.

The soil insecticides of the present invention include, but are not limited to, Abamectin, Acephate, Acequinocyl, Acetamiprid, Acrinathrin, Agrigata, Alanycarb, Aldicarb, Alphacypermethrin, Al-phosphide, Amblyseius, Amitraz, Aphelinus, *Aphidius*, Aphidoletes, Artimisinin, *Autographa californica* NPV, Azadirachtin, Azinphos-m, Azocyclotin, Bacillus-subtilis, Bacillus-thur.-aizawai, Bacillus-thur.-kurstaki, Bacillus-thuringiensis, Beauveria, Beauveria-bassiana, Benfuracarb, Bensultap, Betacyfluthrin, Betacypermethrin, Bifenazate, Bifenthrin, Biologicals, Bispyribac-sodium, Bistrifluron, Bisultap, Brofluthrinate, Bromophos-e, Bromopropylate, Bt-Corn-GM, Bt-Soya-GM, Buprofezin, Cadusafos, Calcium-cyanamide, Capsaicin, Carbaryl, Carbofuran, Carbosulfan, Cartap, *Celastrus*-extract, Chlorantraniliprole, Chlorbenzuron, Chlorethoxyfos, Chlorfenapyr, Chlorfenvinphos, Chlorfluazuron, Chloropicrin, Chlorpyrifos, Chlorpyrifos, Chlorpyrifos-e, Chlorpyrifos-m, Chromafenozide, Clofentezine, Clothianidin, Cnidiadin, Cryolite, Cyanophos, Cyantraniliprole, Cyenopyrafen, Cyflumetofen, Cyfluthrin, Cyhalothrin, Cyhexatin, Cypermethrin, Cyromazine, Cytokinin, Dacnusa, Dazomet, Dazomet, DCIP, Deltamethrin, Demeton-S-m, Diafenthiuron, Diazinon, Dichloropropene, Dichlorvos (DDVP), Dicofol, Difluben-zuron, Diglyphus, Diglyphus+Dacnusa, Dimethacarb, Dimethoate, Dinotefuran, Disulfoton, Dithioether, Dodecyl-acetate, Emamectin, Emamectin-benzoate, Encarsia, Endosulfan, EPN, Eretmocerus, Esfenvalerate, Ethion, Ethiprole, Ethoprophos, Ethylene-dibromide, Etofenprox, Etoxazole, Eucalyptol, Fatty-acids, Fatty-acids/Salts, Fenamiphos, Fenazaquin, Fenbutatin-oxide, Fenitrothion, Fenobucarb (BPMC), Fenobucarb (BPMC), Fenoxycarb, Fenpropathrin, Fenpyroximate, Fenthion, Fenvalerate, Fipronil, Flonicamid, Flubendiamide, Flubrocythrinate, Flucythrinate, Flufenoxuron, Flufenzine, Formetanate, Formothion, Fosthiazate, Furathiocarb, Gamma-cyhalothrin, Garlic-juice, Granulosis-virus, *Harmonia, Heliothis armigera* NPV, Hexaflumuron, Hexythiazox, Imicyafos, Imidacloprid, Inactive bacterium, Indol-3-ylbutyric acid, Indoxacarb, Iodomethane, Iprodione, Iron, Isazofos, Isazofos, Isocarbofos, Isofenphos, Isofenphos-m, Isoprocarb, Isothioate, Isoxathion, Kaolin, Lambda-cyhalothrin, Lepimectin, Lindane, Liuyangmycin, Lufenuron, Malathion, Matrine, Mephosfolan, Metaflumizone, Metaldehyde, Metam-potassium, Metam-sodium, Metarhizium-anisopliae, Methamidophos, Methidathion, Methiocarb, Methomyl, Methoxyfenozide, Methyl-bromide, Metolcarb (MTMC), Mevinphos, Milbemectin, Mineral-oil, Mirex, M-isothiocyanate, Monocrotophos, Monosultap, *Myrothecium verrucaria*, Naled, *Neochrysocharis formosa*, Nicotine, Nitenpyram, Novaluron, Oil, Oleic-acid, Omethoate, Orius, Other pyrethroids, Oxamyl, Oxydemeton-m, Oxymatrine, *Paecilomyces*, Paraffin-oil, Parathion-e, Parathion-m, Pasteuria, Permethrin, Petroleum-oil, Phenthoate, Pheromones, Phorate, Phosalone, Phosmet, Phosphamidon, Phosphorus-acid, *Photorhabdus*, Phoxim, Phytoseiulus, Piperonyl-butoxide, Pirimicarb, Pirimiphos-e, Pirimiphos-m, Plant-oil, *Plutella xylostella* GV, Polyhedrosis-virus, Polyphenol-extracts, Potassium-oleate, Profenofos, Propargite, Propoxur, Prosuler, Prothiofos, Pymetrozine, Pyraclofos, Pyrethrins, Pyridaben, Pyridalyl, Pyridaphenthion, Pyrifluquinazon, Pyrimidifen, Pyriproxifen, Quillay-extract, Quinalphos, Quinomethionate, Rape-oil, Rotenone, Saponin, Saponozit, Silafluofen, Sodium-compounds, Sodium-fluosilicate, Spinetoram, Spinosad, Spirodiclofen, Spiromesifen, Spirotetramat, Starch, Steinernema, *Streptomyces*, Sulfluramid, Sulfoxaflor, Sulphur, Tau-fluvalinate, Tebufenozide, Tebufenpyrad, Tebupirimfos, Teflubenzuron, Tefluthrin, Temephos, Terbufos, Tetradifon, Thiacloprid, Thiamethoxam, Thiocyclam, Thiodicarb, Thiofanox, Thiometon, Thiosultap-sodium, Tolfenpyrad, Tralomethrin, Triazamate, Triazophos, Trichlorfon, Trichlorfon, *Trichoderma*, Trichogramma, Triflumuron, Unknown, Unknown-bioinsecticide, Unknown-insect, *Verticillium*, Vertrine, and Zeta-cypermethrin.

In various embodiments, the soil insecticides can be Corn Insecticides including Chlorpyrifos-e, Cypermethrin, Tefluthrin, Imidacloprid, Bifenthrin, Chlorantraniliprole, Thiodicarb, Tebupirimfos, Carbofuran, Fipronil, Zeta-cypermethrin, Terbufos, Phorate, Acetamiprid, Thiamethoxam, Carbosulfan, and Chlorethoxyfos. Potato Insecticides including Imidacloprid, Oxamyl, Thiamethoxam, Chlorpyrifos-e, Chlorantraniliprole, Carbofuran, Fipronil, Acetamiprid, Ethoprophos, Tefluthrin, Clothianidin, Fenamiphos, Phorate, Bifenthrin, Carbosulfan, Cadusafos, and Terbufos. Soybean Insecticides including Chlorantraniliprole, Thiamethoxam, Flubendiamide, Imidacloprid, Chlorpyrifos-e, Bifenthrin, Thiodicarb, Fipronil, Cypermethrin, Acetamiprid, Carbosulfan, Carbofuran, and Phorate. Sugarcane Insecticides: Fipronil, Imidacloprid, Thiamethoxam, Chlorantraniliprole, Ethiprole, Carbofuran, Chlorpyrifos-e, Cadusafos, Phorate, Terbufos, Bifenthrin, Abamectin, Carbosulfan, Cypermethrin, Oxamyl, and Acetamiprid. Tomato Insecticides including Chlorantraniliprole, Imidacloprid, Thiamethoxam, Chlorpyrifos-e, Acetamiprid, Oxamyl, Flubendiamide, Carbofuran, Bifenthrin, Zeta-cypermethrin, Cadusafos, and Tefluthrin. Vegetable Crop Insecticides including Abamectin, Chlorantraniliprole, Imidacloprid, Chlorpyrifos-e, Acetamiprid, Thiamethoxam, Flubendiamide, Cypermethrin, Fipronil, Oxamyl, Bifenthrin, Clothianidin, Tefluthrin, Terbufos, Phorate, Cadusafos, and Carbosulfan. Banana Insecticide including Oxamyl, Chlorpyrifos-e, Terbufos, Cadusafos, Carbofuran, Ethoprophos, Acetamiprid, Cypermethrin, Bifenthrin, Fipronil, and Carbosulfan.

In some embodiments, the soil insecticide can be one or a combination of bifenthrin, pyrethroids, bifenthrin, tefluthrin, organophosphates, chlorethoxyphos, chlorpyrifos, tebupirimphos, cyfluthrin, fiproles, fipronil, nicotinoids, or clothianidin. In embodiments, the insecticide can be bifenthrin and the composition formulation can further comprise a hydrated aluminum-magnesium silicate, and at least one dispersant selected from the group consisting of a sucrose ester, a lignosulfonate, an alkylpolyglycoside, a naphthalenesulfonic acid formaldehyde condensate and a phosphate ester.

In certain embodiments, the rate of application of the bifenthrin insecticide can be in the range of from about 0.1 gram of bifenthrin per hectare (g ai/ha) to about 1000 g ai/ha, more preferably in a range of from about 1 g ai/ha to about 100 g ai/ha.

In one embodiment of the present invention a composition is provided for benefiting plant growth, the composition comprising: a biologically pure culture of *Bacillus* sp. D747 strain deposited as FERM BP-8234 and a bifenthrin insecticide in a formulation compatible with a liquid fertilizer, wherein each of the *Bacillus* sp. D747 and the bifenthrin insecticide is present in an amount suitable to benefit plant growth.

In another embodiment of the present invention a composition is provided for benefiting plant growth, the composition comprising a biologically pure culture of the *Bacillus* sp. D747 having properties beneficial to plant growth and one or more microbial or chemical pesticide, in a formulation compatible with a liquid fertilizer, wherein the bacterial strain and the one or more microbial or chemical pesticide is present in an amount suitable to benefit plant growth. The chemical pesticide can be an insecticide as listed above. The chemical pesticide can be a fungicide. The chemical pesticide can be an herbicide. The chemical pesticide can be a nematicide. The composition can be in the form of a liquid, a dust, a spreadable granule, a dry wettable powder, or a dry wettable granule. The bacterial strain can be in the form of spores or vegetative cells. The composition can include any combination of insecticide, fungicide, herbicide and/or nematicide.

In one embodiment, the pesticide is a fungicide and can be selected from the group consisting of: B0) benzovindiflupyr, anitiperonosporic, ametoctradin, amisulbrom, copper salts (e.g., copper hydroxide, copper oxychloride, copper sulfate, copper persulfate), boscalid, thiflumazide, flutianil, furalaxyl, thiabendazole, benodanil, mepronil, isofetamid, fenfuram, bixafen, fluxapyroxad, penflufen, sedaxane, coumoxystrobin, enoxastrobin, flufenoxystrobin, pyraoxystrobin, pyrametostrobin, triclopyricarb, fenaminstrobin, metominostrobin, pyribencarb, meptyldinocap, fentin acetate, fentin chloride, fentin hydroxide, oxytetracycline, chlozolinate, chloroneb, tecnazene, etridiazole, iodocarb, prothiocarb, *Bacillus subtilis* syn., *Bacillus amyloliquefaciens* (e.g., strains QST 713, FZB24, MBI600, D747), extract from *Melaleuca alternifolia*, pyrisoxazole, oxpoconazole, etaconazole, fenpyrazamine, naftifine, terbinafine, validamycin, pyrimorph, valifenalate, fthalide, probenazole, isotianil, laminarin, estract from *Reynoutria sachalinensis*, phosphorous acid and salts, teclofthalam, triazoxide, pyriofenone, organic oils, potassium bicarbonate, chlorothalonil, fluoroimide; B1) azoles, including bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thia-bendazole, fuberidazole, ethaboxam, etridiazole and hymexazole, azaconazole, diniconazole-M, oxpoconazol, paclobutrazol, uniconazol, 1-(4-chloro-phenyl)-2-([1,2,4]triazol-1-yl)-cycloheptanol and imazalilsulfphate; B2) strobilurins, including azoxystrobin, dimoxystrobin, enestroburin, fluoxastrobin, kresoximmethyl, methominostrobin, orysastrobin, picoxystrobin, pyraclostrobin, trifloxystrobin, enestroburin, methyl(2-chloro-5-[1-(3-methylbenzyloxyimino)ethyl]benzyl)carbamate, methyl(2-chloro-5-[1-(6-methylpyridin-2-yl-methoxyimino)ethyl]benzyl)carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxyphenyl)-cycl opropanecarboximidoylsulfanylmethyl)-phenyl)-acrylic acid methyl ester; B3) carboxamides, including carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl) prop-2-ynyloxy]-3-methoxyphenyl)ethyl)-2-methanesulfonyl-amino-3-methylbutyramide, N-(2-(4-[3-(4-chloro-phenyl)prop-2-ynyloxy]-3-methoxy-phenyl)ethyl)-2-ethanesulfonylamino-3-methylbutyramide, methyl 3-(4-chlorophenyl)-3-(2-isopropoxycarbonyl-amino-3-methylbutyrylamino)propionate, N-(4'-bromobiphenyl-2-yl)-4-difluoromethyl-methylthiazole-6-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3\4'-dichloro-4-fluorobiphenyl-2-yl)-3-difluoro-methyl-1-methyl-pyrazole-4-carboxamide, N-(3', 4'-dichloro-5-fluorobiphenyl-2-yl)-3-difluoromethyl-1-methylpyrazole-4-carboxamide, N-(2-cyano-phenyl)-3,4-dichloroisothiazole-5-carboxamide, 2-amino-4-methyl-thiazole-5-carboxanilide, 2-chloro-N-(1,1,3-trimethyl-indan-4-yl)-nicotinamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-1H-pyrazole-4-carboxamide, N-(4'-chloro-3',5-difluoro-biphenyl-2-yl)-3-trifluoromethyl-1-methyl-1H-pyrazole-4-carboxamide, N-(3',4'-dichloro-5-fluoro-biphenyl-2-yl)-3-trifluoromethyl-1-methyl-1H-pyrazole-4-carboxamide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-ylphenyl)-3-difluoro-methyl-1-methyl-1H-pyrazole-4-carboxamide, fluopyram, N-(3-ethyl-3,5-5-trimethyl-cyclohexyl)-3-formylamino-2-hydroxy-benzamide, oxytetracyclin, silthiofamn, N-(6-methoxy-pyridin-3-yl)cyclopropanecarboxamide, 2-iodo-N-phenyl-benzamide, N-(2-bicyclo-propyl-2-yl-phenyl)-3-difluormethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-ylcarboxamide, N-(3',4',5'-trifluorobiphenyl-2-yl)-5-chloro-1,3-dimethyl-pyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3',4',5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazole-4-carboxamide, N-(3',4'-dichloro-3-fluorobiphenyl-2-yl)-1-methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-S-difluoromethyl-1H-pyrazole-4-carboxamide, N-(3'-chloro-4'-fluoro-3-fluorobiphenyl-2-yl)-1-methyl-3-difluoromethyl-1H-pyrazole-4-carboxamide, N-(3',4'-dichloro-4-fluorobiphenyl-2-yl)-1-methyl-3-trifluoromethyl-1H-pyrazole-4-carboxamide, N-(3',4'-difluoro-4-fluorobiphenyl-2-yl)-1-methyl-S-trifluoromethyl-1H-pyrazole-4-carboxamide, N-(3',4'-dichloro-4-fluorobiphenyl-2-yl)-1-methyl-3-difluoromethyl-1H-pyrazole-4-carboxamide, N-(3',4'-difluoro-4-fluorobiphenyl-2-yl)-1-methyl-3-difluoromethyl-1H-pyrazole-4-carboxamide, N-(3'-chloro-4'-fluoro-4-fluorobiphenyl-2-yl)-1-methyl-S-difluoromethyl-1H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4'-dichloro-5-fluorobiphenyl-2-yl)-1-methyl-S-difluoromethyl-1H-pyrazole-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide, N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1,3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide, N-(4'-chloro-6-fluorobiphenyl-2-yl)-1-methyl-3-trifluoromethyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[4'-(trifluoromethylthio)-biphenyl-2-yl]-3-difluoromethyl-1-methyl-1H-pyrazole-4-carboxamide and N-[4'-(trifluoromethylthio)-biphenyl-2-yl]-1-methyl-3-trifluoromethyl-1-methyl-1H-pyrazole-4-carboxamide; B4) heterocyclic compounds, including fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methyl-piperidin-1-yl)-6-(2,4,6-trifluorophenyl)-[1,2,4]triazolo[1,5-a]pyrimidine, anilazine, diclomezine, pyroquilon, proquinazid, tricyclazole, 2-butoxy-6-iodo-3-propylchromen-4-one, acibenzolar-S-methyl, captafol, captan, dazomet, folpet, fenoxanil, quinoxyfen, N,N-dimethyl-3-(3-bromo-6-fluoro-2-methylindole-1-sulfonyl)-[1,2,4]triazole-1-sulfonamide, 5-ethyl-6-octyl-[1,2,4]triazolo[1,5-a]pyrimidin-2,7-diamine, 2,3,5,6-tetrachloro-4-methanesulfonyl-pyridine, 3,4,5-trichloro-pyridine-2,6-dicarbonitrile, N-(1-(5-bromo-3-chloro-pyridin-2-yl)-ethyl)-2,4-dichloro-nicotinamide, N-((5-bromo-3-chloro pyridin-2-yl)-methyl)-2,4-dichloro-nicotinamide, diflumetorim, nitrapyrin, dodemorphacetate, fluoroimid, blasticidin-S, chinomethionat, debacarb, difenzoquat, difenzoquat-methylsulphat, oxolinic acid and piperalin; B5) carbamates, including mancozeb, maneb, metam, methasulphocarb, metiram, ferbam, propineb, thiram, zineb, ziram, diethofencarb, iprovalicarb, benthiavalicarb, propamocarb, propamocarb hydrochlorid, 4-fluorophenyl N-(1-(1-(4-cyanophenyl)-ethanesulfonyl)but-2-yl)carbamate, methyl 3-(4-chloro-phenyl)-3-(2-isopropoxycarbonylamino-3-methyl-butyrylamino)propanoate; or B6) other fungicides, including guanidine, dodine, dodine free base, iminoctadine, guazatine, antibiotics: kasugamycin, oxytetracyclin and its salts, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts, organophosphorus compounds: edifenphos, iprobenfos, fosetyl, fosetyl-aluminum, phosphorous acid and its salts, pyrazophos, tolclofos-methyl, organochlorine compounds: dichlofluanid, flusulfamide, hexachloro-benzene, phthalide, pencycuron, quintozene, thiophanate, thiophanate-methyl, tolylfluanid, others: cyflufenamid, cymoxanil, dimethirimol, ethirimol, furalaxyl, metrafenone and spiroxamine, guazatine-acetate, iminoc-tadine-triacetate, iminoctadine-tris(albesilate), kasugamycin hydrochloride hydrate, dichlorophen, pentachlorophenol and its salts, N-(4-chloro-2-nitro-phenyl)-N-ethyl-4-methyl-benzenesulfonamide, dicloran, nitrothal-isopropyl, tecnazen, biphenyl, bronopol, diphenylamine, mildiomycin, oxincopper, prohexadione calcium, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethylsilanyl-propoxy)-phenyl)-N-ethyl-N-methylformamidine and N'-(5-difluormethyl-2-methyl-4-(3-trimethylsilanyl-propoxy)-phenyl)-N-ethyl-N-methyl formamidine.

In one embodiment, the pesticide is a herbicide is selected from the group consisting of: C1) acetyl-CoA carboxylase inhibitors (ACC), for example cyclohexenone oxime ethers, such as alloxydim, clethodim, cloproxydim, cycloxydim, sethoxydim, tralkoxydim, butroxydim, clefoxydim or tepraloxydim; phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or arylaminopropionic acids, such as flamprop-methyl or flamprop-isopropyl; C2 acetolactate synthase inhibitors (ALS), for example imidazolinones, such as imazapyr, imazaquin, imazamethabenz-methyl(imazame), imazamox, imazapic or imazethapyr; pyrimidyl ethers, such as pyrithiobac-acid, pyrithiobac-sodium, bispyribac-sodium. KIH-6127 or pyribenzoxym; sulfonamides, such as florasulam, flumetsulam or metosulam; or sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron; C3) amides, for example allidochlor (CDAA), benzoylprop-ethyl, bromobutide, chiorthiamid, diphenamid, etobenzanidibenzchlomet), fluthiamide, fosamin or monalide; C4) auxin herbicides, for example pyridinecarboxylic acids, such as clopyralid or picloram; or 2,4-D or benazolin; C5) auxin transport inhibitors, for example naptalame or diflufenzopyr; C6) carotenoid biosynthesis inhibitors, for example benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol; C7) enolpyruvylshikimate-3-phosphate synthase inhibitors (EPSPS), for example glyphosate or sulfosate; C8) glutamine synthetase inhibitors, for example bilanafos (bialaphos) or glufosinate-ammonium; C9) lipid biosynthesis inhibitors, for example anilides, such as anilofos or mefenacet; chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor; thioureas, such as butylate, cycloate, di-allate, dimepiperate, EPTC. esprocarb, molinate, pebulate, prosulfocarb, thiobencarb (benthiocarb), tri-allate or vemolate; or benfuresate or perfluidone; C10) mitosis inhibitors, for example carbamates, such as asulam, carbetamid, chlorpropham, orbencarb, pronamid (propyzamid), propham or tiocarbazil; dinitroanilines, such as benefin, butralin, dinitramin, ethalfluralin, fluchloralin, oryzalin, pendimethalin, prodiamine or trifluralin; pyridines, such as dithiopyr or thiazopyr; or butamifos, chlorthal-dimethyl (DCPA) or maleic hydrazide; C11) protoporphyrinogen IX oxidase inhibitors, for example diphenyl ethers, such as acifluorfen, acifluorfen-sodium, aclonifen, bifenox, chlomitrofen (CNP), ethoxyfen, fluorodifen, fluoroglycofen-ethyl, fomesafen, furyloxyfen, lactofen, nitrofen, nitrofluorfen or oxyfluorfen; oxadiazoles, such as oxadiargyl or oxadiazon; cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or pyrazoles, such as ET-751.JV 485 or nipyraclofen; C12) photosynthesis inhibitors, for example propanil, pyridate or pyridafol; benzothiadiazinones, such as bentazone; dinitrophenols, for example bromofenoxim, dinoseb, dinoseb-acetate, dinoterb or DNOC; dipyridylenes, such as cyperquatchloride, difenzoquat-methylsulfate, diquat or paraquatdichloride; ureas, such as chlorbromuron, chlorotoluron, difenoxuron, dimefuron, diuron, ethidimuron, fenuron, flumeturon, isoproturon, isouron, linuron, methabenzthiazuron, methazole, metobenzuron, metoxuron, monolinuron, neburon, siduron or tebuthiuron; phenols, such as bromoxynil or ioxynil; chloridazon; triazines, such as ametryn, atrazine, cyanazine, desmein, dimethamethryn, hexazinone, prometon, prometryn, propazine, simazine, simetryn, terbumeton, terbutryn, terbutylazine or trietazine; triazinones, such as metamitron or metribuzin; uracils, such as bromacil, lenacil or terbacil; or biscarbamates, such as desmedipham or phenmedipham; C13) synergists, for example oxiranes, such as tridiphane; C14) CIS cell wall synthesis inhibitors, for example isoxaben or dichlobenil; C16) various other herbicides, for example dichloropropionic acids, such as dalapon; dihydrobenzofurans, such as ethofumesate; phenylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon; and their environmentally compatible salts.

In another embodiment, the chemical pesticide in the composition is a nematicide selected from the group consisting of: benomyl, cloethocarb, aldoxycarb, tirpate, diamidafos, fenamiphos, cadusafos, dichlofenthion, ethoprophos, fensulfothion, fosthiazate, heterophos, isamidofof, isazofos, phosphocarb, thionazin, imicyafos, mecarphon, acetoprole, benclothiaz, chloropicrin, dazomet, fluensulfone, 1,3-dichloropropene (telone), dimethyl disulfide, metam sodium, metam potassium, metam salt (all MITC generators), methyl bromide, soil amendments (e.g., mustard seeds, mustard seed extracts), steam fumigation of soil, allyl isothiocyanate (AITC), dimethyl sulfate, and furfual (aldehyde).

In another embodiment, a method for benefiting plant growth is provided comprising delivering to a plant in a liquid fertilizer a composition comprising a soil insecticide and a biologically pure culture of *Bacillus* sp. D747 strain having properties beneficial to plant growth wherein the composition is delivered in the liquid fertilizer in an amount suitable for benefiting plant growth to: seed of the plant, roots of the plant, a cutting of the plant, a graft of the plant, callus tissue of the plant, soil or growth medium surrounding the plant, soil or growth medium before sowing seed of the plant in the soil or growth medium, or soil or growth medium before planting the plant, the plant cutting, the plant graft, or the plant callus tissue in the soil or growth medium.

In certain embodiments, the present invention is directed to compositions comprising bifenthrin; a biologically pure culture of *Bacillus* sp. D747 strain deposited as FERM BP-8234; a hydrated aluminum-magnesium silicate; and at least one dispersant selected from a sucrose ester, a lignosulfonate, an alkylpolyglycoside, a naphthalenesulfonic acid formaldehyde condensate and a phosphate ester. In some embodiments, the composition is an aqueous based suspension. In another embodiment a second chemical pesticide is included in the composition selected from the group fungicides, herbicides and nematicides.

In some embodiments, bifenthrin is preferably present in a concentration of from about 1.0% by weight to about 50% by weight, or from about 15% by weight to about 25% by weight, based upon the total weight of all components in the composition. In some embodiments, the bifenthrin is present in a concentration of about 17% to about 18% by weight, based upon the total weight of all components in the composition.

In some embodiments, the hydrated aluminum-magnesium silicate is selected from the group consisting of montmorillonite and attapulgite.

In some embodiments, the phosphate ester is selected from a nonyl phenol phosphate ester and a tridecyl alcohol ethoxylated phosphate potassium salt.

In some embodiments, water is present in the composition at from about 25% to about 75%, or from about 35% to about 50% by weight, based upon the total weight of all components in the composition.

In some embodiments, the composition comprises about 1% to about 20% of hydrated aluminum-magnesium silicate, based upon the total weight of all components in the composition.

In some embodiments, the composition comprises about 0.2% to about 20% of at least one dispersant, based upon the total weight of all components in the composition.

In some embodiments, a biological control agent is present in the composition comprising from about $7.6 \times 10^9$ CFU/ml to about $1.2 \times 10^{10}$ CFU/ml of a biologically pure culture of the *Bacillus* sp. D747 strain deposited as FERM BP-8234.

In some embodiments, the a biologically pure culture of the *Bacillus* sp. D747 strain deposited as FERM BP-8234 can be in the form of spores or in the form of vegetative cells.

In one embodiment, the composition comprises: from about 15% to 25% of bifenthrin; from about $7.6 \times 10^9$ CFU/ml to about $1.2 \times 10^{10}$ CFU/ml of a biologically pure culture of the *Bacillus* sp. D747 strain deposited as FERM BP-8234; from about 1% to about 20% of hydrated aluminum-magnesium silicate; from about 0.2% to about 20% of at least one dispersant selected from a sucrose ester, a lignosulfonate, an alkylpolyglycoside, a naphthalenesulfonic acid formaldehyde condensate and a phosphate ester; and from about 35% to about 50% water; wherein all % are % by weight based upon the total weight of all components in the composition.

In addition to compositions in which the composition comprising the *Bacillus* sp. D747 strain deposited as FERM BP-8234 and the bifenthrin insecticide are formulated together, a product composition for benefiting plant growth is also provided in the present invention that includes these two compositions packaged as two separate components. Specifically, the product includes a first component including a first composition comprising a biologically pure culture of the *Bacillus* sp. D747 strain deposited as FERM BP-8234; a second component comprising a second composition comprising a bifenthrin insecticide, wherein the first and second components are separately packaged; and instructions for delivering a plant growth effective amount of a combination of the first and second compositions to plant propagation material. In some embodiments, the plant propagation material is selected from seeds, spores, bulbs, cuttings, sets, rhizomes, tubers, meristem tissue, plant cells, and combinations thereof. In embodiments, the bifenthrin composition may comprise: bifenthrin; a hydrated aluminum-magnesium silicate; and at least one dispersant selected from a sucrose ester, a lignosulfonate, an alkylpolyglycoside, a naphthalenesulfonic acid formaldehyde condensate and a phosphate ester.

Table 1 below provides exemplary formulations according to certain embodiments of the invention.

TABLE 1

| Ingredients | w/w % as is | Preferred Ranges Approximate w/w % as is | Approximate w/w % as is |
|---|---|---|---|
| Bifenthrin technical | 17.64% | | |
| BaD747 | 5.00% | 0.10 | 15.0 |
| Agnique PG 9116 | 8.00% | 1.00 | 15.0 |
| Dextrol OC-180 | 7.00% | 1.00 | 15.0 |
| Attaflow FL | 9.00% | 7.00 | 13.0 |
| Sodium benzoate | 0.10% | 0.00 | 0.2 |
| Potassium sorbate | 0.10% | 0.00 | 0.2 |
| Ammonium sulfate | 9.50% | 7.00 | 18.0 |
| Acetic Acid | 0.10% | 0.00 | 3.0 |
| Xiameter AFE-0100 | 0.10% | 0.10 | 0.5 |
| DI Water | 30.00% | | |
| Holdback DI | 13.46% | | |
| Total | 100.00% | | |

Some embodiments further include a liquid fertilizer. In embodiments, the composition can be formulated in a manner suitable for mixture as a liquid with a fertilizer. The product can further include a separately packaged fertilizer.

Other embodiments further include at least one of an anti-freeze agent, an anti-foam agent and a biocide.

As is employed herein the term "plant propagation material" includes plant seeds, spores, bulbs, cuttings (e.g. stems, roots, leaves, and the like), sets, rhizomes, tubers, meristem tissue, single and multiple plant cells, and any other plant tissue from which a complete plant can be obtained.

The compositions according to embodiments of the present invention may be applied to the propagative material by any means, including direct application, as a seed treatment, in furrow or band applications, by means well known to those in the art.

In some embodiments, the composition includes bifenthrin; a biologically pure culture of *Bacillus* sp. D747 strain deposited as FERM BP-8234; a hydrated aluminum-magnesium silicate; at least one dispersant selected from a sucrose ester, a lignosulfonate, an alkylpolyglycoside, a naphthalenesulfonic acid formaldehyde condensate and a phosphate ester; and a liquid fertilizer. The term "liquid fertilizer" refers to a fertilizer in a fluid or liquid form containing various ratios of nitrogen, phosphorous and potassium (for example, but not limited to, 10% nitrogen, 34% phosphorous and 0% potassium) and micronutrients, commonly known as starter fertilizers that are high in phosphorus and promote rapid and vigorous root growth. In embodiments, the liquid fertilizer is present in a concentration of from about 95.00% by weight to about 99.99% by weight based upon the total weight of all components in the formulation.

Optionally, the composition may further include at least one of an anti-freeze agent, an anti-foam agent and a biocide. These formulation components are well-known in the agrochemical arts. In one embodiment, the anti-freeze agent is a polyalkylene glycol, preferably propylene glycol, and when present, is present in an amount from about 5% to about 9% by weight of the total of all components in the composition. In one embodiment, the anti-foam agent is an alkylcyclotetrasiloxane, preferably an octamethylcyclo-tetrasiloxane silicone emulsion, for example, DOW CORNING® AF Emulsion or DOWCORNING® ANTIFOAM C Emulsion (available from Dow Corning Corporation). When present, the anti-foam agent is preferably present in an amount of from about 0.001% to about 1% by weight of all the components in the total formulation. The preservative can be an isothiazolone or a mixture of isothiazolones, for example, KATHON® CG/ICP preservative or LEGEND® MK preservative (available from Rohm and Haas Corporation) or PROXEL™ BR preservative (available from Avecia Corporation). When present, the preservative is preferably present in an amount of from about 0.001% to about 1% by weight of the total of all components in the formulation.

In certain embodiments, a process is provided for preparing a composition of this invention comprising dispersing bifenthrin in a mixture of water and at least one dispersant, and optionally, an anti-freeze agent, an anti-foam agent and/or a biocide; wet milling the mixture, adding a hydrated aluminum-magnesium silicate and blending the mixture. To the blended mixture is added *Bacillus* sp. D747. In some embodiments, the *Bacillus* sp. D747 may be in the form of a dry powder. In some embodiments, the *Bacillus* sp. D747 may be in the form of spores. The process may further comprise adding the resultant mixture to a liquid fertilizer.

In some embodiments, the present invention also encompasses a method of controlling plant diseases, including, but not limited to, fungal diseases of plants, the method comprising applying to an area containing such plants an effective amount of a liquid fertilizer in combination with a composition according to an embodiment of the invention.

Some embodiments provide a method of improving the growth of a plant by applying a plant growth effective amount a composition according to the present invention to plant propagation material. In some embodiments, the plant propagation material is selected from seeds, spores, bulbs, cuttings, sets, rhizomes, tubers, meristem tissue, plant cells, and combinations thereof. In some embodiments, the plant propagation material includes at least one seed.

In some embodiments, the composition is applied at a rate ranging from about 0.1 g/ha to about 1000 gm/ha.

In some embodiments, the method further includes applying a liquid fertilizer to: soil or growth medium surrounding the plant; soil or growth medium before sowing seed of the plant in the soil or growth medium; or soil or growth medium before planting the plant, the plant cutting, the plant graft, or the plant callus tissue in the soil or growth medium. The term "liquid fertilizer" refers to a fertilizer in a fluid or liquid form containing various ratios of nitrogen, phosphorous and potassium (for example, but not limited to, 10% nitrogen, 34% phosphorous and 0% potassium) and micronutrients, commonly known as starter fertilizers that are high in phosphorus and promote rapid and vigorous root growth.

All references cited herein are incorporated by reference herein in their entireties.

The following examples serve to further illustrate the present invention.

Example 1

This example illustrates the preparation of a composition comprising bifenthrin and *Bacillus* sp. D747 strain deposited as FERM BP-8234.

Into a CMC SuperMill feed tank was added 4.9935 kilograms of deionized water, 1.3316 kilograms of a C9-11 alkyl polyglycoside (AGNIQUE® PG 9116, available from Cognis), 1.1651 kilograms of an ethoxylated aliphatic alcohol phosphate ester potassium salt (Dextrol™ OC-180, available from Ashland Specialty Ingredients), 16.6 grams of an anti-foam agent (XIAMETER@AFE-0100 Antifoam Emulsion FG, available from Dow Corning Corporation), 16.6 grams of sodium benzoate, 1606 grams of potassium sorbate and 1.5813 kilograms of ammonium sulfate. The mill was started and the contents were mixed until uniform. Crystalline bifenthrin technical (97.2% purity) was added portion wise and after complete addition the contents mixed for about one hour. The contents of the feed tank was transferred to the mill, keeping the mill temperature at 40° F., and milled until a particle size of about 7 microns (D90) was obtained. Once the desired particle size was obtained, 1.0 kilogram of deionized water was added to the feed tank and pumped through the mill contents. A liquid attapulgite suspension aid, 1.498 kilograms of ATTAFLOW® FL (available from BASF The Chemical Company) was added and the mixture blended until uniform. Acetic acid, 16.6 grams, was added and incorporated until homogenous. *Bacillus* sp. strain D747 (available from Certis USA), 832.2 grams of a dry powder containing at least $2\times10^{11}$ CFU *bacillus* spores, was added and the mixture stirred until homogenous.

Portions of the bifenthrin/*bacillus* formulation were stored in sealed glass containers for stability testing. Table 2 summarizes the initial and monthly spore viability was measured on samples kept at 25° C. Samples stored at room temperature or 35° C. were analyzed at 1, 2, and 3 months and found to be physically and chemically stable at each time period. A sample stored at 54° C. for two weeks was found to be physically and chemically stable. Another sample was subjected to three freeze and thaw cycles and found to be physically and chemically stable.

TABLE 2

*Bacillus* sp. strain D747 viability testing of samples stored at 25° C.
CFU/mL

| Time 0 | 22 Days | 52 Days | 83 Days | 113 Days | 147 Days | 177 Days |
|---|---|---|---|---|---|---|
| $1.2 \times 10^{10}$ | $1.1 \times 10^{10}$ | $1.2 \times 10^{10}$ | $1.2 \times 10^{10}$ | $1.2 \times 10^{10}$ | $1.2 \times 10^{10}$ | $1.4 \times 10^{10}$ |

As can be seen from the data in Table 2, the *Bacillus* spores in the formulation remain viable after 177 days storage at 25° C.

Example 2

Comparative Stability Studies

The physical stability of the formulation of Example 1 was tested by mixing the formulation with an 11% nitrogen-37% phosphorous-0% potassium liquid fertilizer at a 5% to 95% weight ratio and observing the mixture's physical stability in a 500 milliliter/50 cm chromatography column. The stability of the formulation of Example 1 was compared with that of an Emulsifiable Concentrate (EC) of bifenthrin (TALSTAR® 2 EC, available from FMC Corporation) that was mixed at a 5% to 95% by weight with an 11-37-0 liquid fertilizer. To a glass cylinder were added 95 grams of an 11-37-0 liquid fertilizer and 5 grams of the Example 1 composition or TALSTAR® 2 EC. The glass cylinder was sealed and inverted 30 times to mix the components. The test mixture was poured into a glass chromatography column and a 10 ml sample was withdrawn at 10 minute intervals. The samples were analyzed by HPLC to determine the amount of bifenthrin in each sample in parts per million. Table 3 below contains the results of the stability test.

TABLE 3

Physical Stability of Compositions Containing Bifenthrin In High Phosphate Liquid Fertilizer

| Test Composition | Concentration of Bifentinin (ppm In Samples Taken At The Elapsed Time (minutes) | | | | | |
|---|---|---|---|---|---|---|
|  | 0 | 10 | 20 | 30 | 40 | 50 |
| Example 1 | 7260 | 7060 | 6820 | 6960 | 6390 | 7160 |
| TALSTAR ® 2 EC | 9427 | 7557 | 7052 | 5630 | 4270 | 2984 |

The test data provided in Table 2 indicate that the formulation of Example 1 is homogenous throughout the test indicating good physical stability, whereas TALSTAR® 2 EC is not homogenous and has poor physical stability.

Example 3

This example illustrates the preparation of a composition comprising bifenthrin and *Bacillus* sp. D747 strain deposited as FERM BP-8234.

A mixture of 233.80 grams of deionized water, 40.00 grams of a C9-11 alkyl polyglycoside (Agnique® PG 9116, available from Cognis), 35 grams of an ethoxylated aliphatic alcohol phosphate ester potassium salt (DEXTROI™ OC-180, available from Ashland Specialty Ingredients), 0.50 grams of an anti-foam agent (DOWCORNING® AF Emulsion, available from Dow Corning Corporation), 47.50 grams of propylene glycol, 50.00 grams of liquid attapulgite suspension aid (ATTAFLOW® FL, available from BASF The Chemical Company) and 88.22 grams of crystalline bifenthrin technical (97.2% purity) was stirred in a glass container using an overhead stirrer for 30 minutes. The mixture was homogenized using a Silverson rotor/stator for three minutes. The mixture was transferred to an Eiger Mini Mill set at 3,000 rpm for 30 minutes. The mixture was transferred to a glass container and was homogenized with a Polytron homoginizer at 6,000 rpm. The homogenizer was removed and 5.00 grams of *Bacillus* sp. strain D747, as a dry powder containing at least $2\times10^{11}$ CFU *bacillus* spores was added. The mixture was stirred slowly for about 30 minutes providing a completely homogenous mixture. Portions of the bifenthrin/*bacillus* formulation were stored in sealed glass containers for stability testing. Table 4 summarizes the initial and monthly spore viability measured for samples kept at 25° C.

TABLE 4

*Bacillus* sp. strain D747 viability testing of samples stored at 25° C.

| | Time 0 | 2 Months | 3 Months | 4 Months | 5 Months | 6 Months | 7 Months | 8 Months |
|---|---|---|---|---|---|---|---|---|
| CFU/mL | $7.7 \times 10^9$ | $7.8 \times 10^9$ | $6.0 \times 10^9$ | $7.3 \times 10^9$ | $7.8 \times 10^9$ | $7.4 \times 10^9$ | $8.6 \times 10^9$ | $6.4 \times 10^9$ |

As can be seen from the data in Table 4, the *Bacillus* spores in the formulation remain viable after 8 months storage at 25° C.

While this invention has been described with an emphasis upon preferred embodiments, it will be obvious to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the claims that follow.

What is claimed is:

1. A homogeneous composition for benefiting plant growth, the composition comprising:
   a biologically pure culture of *Bacillus* sp. D747 strain having properties beneficial to plant growth and one or more chemical pesticides comprising bifenthrin, tefluthrin, zeta-cypermethrin or cyfluthrin, in a formulation compatible with a liquid fertilizer, wherein said strain and the one or more chemical pesticide are present in an amount suitable to benefit plant growth; wherein the inclusion of said strain increases the physical stability of the one or more chemical pesticides.

2. The composition of claim 1, wherein the *Bacillus* sp. D747 is deposited as FERM BP-8234.

3. The composition of claim 1, wherein the chemical pesticide comprises an insecticide, a fungicide, an herbicide, or a nematicide.

4. The composition of claim 1, wherein the strain is in the form of spores or vegetative cells.

5. The composition of claim 1, wherein the composition is in the form of a liquid, a dust, a spreadable granule, a dry wettable powder, or a dry wettable granule.

6. The composition of claim 2, wherein the biologically pure culture of the *Bacillus* sp. D747 strain deposited as FERM BP-8234 is present at from about $7.6\times10^9$ CFU/ml to about $1.2\times10^{10}$ CFU/ml.

7. The composition of claim 3, wherein the insecticide is one or a combination of soil insecticides selected from the group consisting of pyrethroids, bifenthrin, tefluthrin, zeta-cypermethrin, organophosphates, chlorethoxyphos, chlorpyrifos, tebupirimphos, cyfluthrin, fiproles, fipronil, nicotinoids, and clothianidin.

8. The composition of claim 7, wherein the bifenthrin is present at a concentration ranging from 0.1 g/ml to 0.2 g/ml.

9. A product comprising:
a combining of a first component and a second component the first component comprising a first composition comprising a biologically pure culture of *Bacillus* sp. D747 strain having properties beneficial to plant growth; and the second component comprising a second composition comprising a soil insecticide comprising bifenthrin, tefluthrin, zeta-cypermethrin or cyfluthrin, wherein the first and second components are separately packaged, wherein each component is in a formulation compatible with a liquid fertilizer, and wherein each component is in an amount suitable to benefit plant growth; the combining of the first component and second component forms a homogenous composition wherein the presence of said strain increases the physical stability of the soil insecticide.

10. The product of claim 9, wherein the soil insecticide is one or a combination of pyrethroids, bifenthrin, tefluthrin, zeta-cypermethrin, organophosphates, chlorethoxyphos, chlorpyrifos, tebupirimphos, cyfluthrin, fiproles, fipronil, nicotinoids, or clothianidin.

11. The product of claim 9, wherein the soil insecticide is bifenthrin and the second composition further comprises a hydrated aluminum-magnesium silicate, and at least one dispersant selected from the group consisting of a sucrose ester, a lignosulfonate, an alkylpolyglycoside, a naphthalenesulfonic acid formaldehyde condensate and a phosphate ester.

12. The product of claim 11, wherein the bifenthrin is present at a concentration ranging from 0.1 g/ml to 0.2 g/ml.

13. The product of claim 9, wherein each of the first and second compositions is in the form of a liquid, a dust, a spreadable granule, a dry wettable powder, or a dry wettable granule.

14. The product of claim 9, wherein the *Bacillus* sp. D747 is deposited as FERM BP-8234.

15. The product of claim 14, wherein the biologically pure culture of the *Bacillus* sp. D747 strain deposited as FERM BP-8234 is present at from about $7.6 \times 10^9$ CFU/ml to about $1.2 \times 10^{10}$ CFU/ml.

16. A method for benefiting plant growth comprising delivering to a homogeneous plant in a liquid fertilizer a composition comprising a biologically pure culture of *Bacillus* sp. D747 strain having properties beneficial to plant growth, and a soil insecticide comprising bifenthrin, tefluthrin, zeta-cypermethrin or cyfluthrin, wherein the composition is delivered in the liquid fertilizer in an amount suitable for benefiting plant growth to: seed of the plant, roots of the plant, a cutting of the plant, a graft of the plant, callus tissue of the plant, soil or growth medium surrounding the plant, soil or growth medium before sowing seed of the plant in the soil or growth medium, or soil or growth medium before planting the plant, the plant cutting, the plant graft, or the plant callus tissue in the soil or growth medium wherein the presence of said strain increases the physical stability of the soil insecticide.

17. The method of claim 16, wherein the plant growth benefit is exhibited by improved seedling vigor, improved root development, improved plant health, increased plant mass, increased yield, improved appearance, improved resistance to osmotic stress, improved resistance to plant pathogens, or combinations thereof.

18. The method of claim 16, wherein the soil insecticide is one or a combination of pyrethroids, bifenthrin, tefluthrin, zeta-cypermethrin, organophosphates, chlorethoxyphos, chlorpyrifos, tebupirimphos, cyfluthrin, fiproles, fipronil, nicotinoids, or clothianidin.

19. The method of claim 16, wherein the strain is in the form of spores or vegetative cells.

20. The method of claim 16, wherein the *Bacillus* sp. D747 is deposited as FERM BP-8234.

21. The method of claim 20, wherein the biologically pure culture of the *Bacillus* sp. D747 strain deposited as FERM BP-8234 is present at from about $7.6 \times 10^9$ CFU/ml to about $1.2 \times 10^{10}$ CFU/ml.

22. The method of claim 16, wherein the plant comprises monocots, dicots, Cereals, Corn, Sweet Corn, Popcorn, Seed Corn, Silage Corn, Field Corn, Rice, Wheat, Barley, Sorghum, *Brassica* Vegetables, Broccoli, Cabbage, Cauliflower, Brussels Sprouts, Collards, Kale, Mustard Greens, Kohlrabi, Bulb Vegetables, Onion, Garlic, Shallots, Fruiting Vegetables, Pepper, Tomato, Eggplant, Ground Cherry, Tomatillo, Okra, Grape, Herbs/Spices, Cucurbit Vegetables, Cucumber, Cantaloupe, Melon, Muskmelon, Squash, Watermelon, Pumpkin, Eggplant, Leafy Vegetables, Lettuce, Celery, Spinach, Parsley, Radicchio, Legumes/Vegetables (succulent and dried beans and peas), Beans, Green beans, Snap beans, Shell beans, Soybeans, Dry Beans, Garbanzo beans, Lima beans, Peas, Chick peas, Split peas, Lentils, Oil Seed Crops, Canola, Castor, Cotton, Flax, Peanut, Rapeseed, Safflower, Sesame, Sunflower, Soybean, Root/Tuber and Corm Vegetables, Carrot, Potato, Sweet Potato, Beets, Ginger, Horseradish, Radish, *Ginseng*, Turnip, sugarcane, sugarbeet, Grass, or Turf grass.

23. A homogeneous composition for benefiting plant growth, the composition comprising: a biologically pure culture of *Bacillus* sp. D747 strain deposited as FERM BP-8234 and bifenthrin in a formulation compatible with a liquid fertilizer, wherein each of the *Bacillus* sp. D747 and the bifenthrin is present in an amount suitable to benefit plant growth wherein the presence of said strain increases the physical stability of bifenthrin.

24. The composition of claim 23 further comprising a hydrated aluminum-magnesium silicate; and at least one dispersant selected from the group consisting of a sucrose ester, a lignosulfonate, an alkylpolyglycoside, a naphthalenesulfonic acid formaldehyde condensate and a phosphate ester.

25. The composition of claim 23, wherein the bifenthrin is present at from about 15% to about 25% by weight based upon the total weight of all components in the composition.

26. The composition of claim 23, wherein the biologically pure culture of the *Bacillus* sp. D747 strain deposited as FERM BP-8234 is present at from about $7.6 \times 10^9$ CFU/ml to about $1.2 \times 10^{10}$ CFU/ml.

27. The composition of claim 24, wherein the hydrated aluminum-magnesium silicate is present at from about 1% to about 20% by weight based upon the total weight of all components in the composition.

28. The composition of claim 24, wherein the dispersant is present from about 0.2% to about 20% by weight based upon the total weight of all components in the composition.

29. The composition of claim 24, wherein the hydrated aluminum-magnesium silicate is selected from the group consisting of montmorillonite and attapulgite, and the phosphate ester is selected from the group consisting of a nonyl phenol phosphate ester and a tridecyl alcohol ethoxylated phosphate potassium salt.

30. The composition of claim 24, wherein the composition comprises:

a) from about 15% to about 25% of bifenthrin;

b) from about $7.6\times10^9$ CFU/ml to about $1.2\times10^{10}$ CFU/ml of a biologically pure culture of the *Bacillus* sp. D747 strain deposited as FERM BP-8234;

c) from about 1% to about 20% of the hydrated aluminum-magnesium silicate;

d) from about 0.2% to about 20% of the at least one dispersant selected from the group consisting of a sucrose ester, a lignosulfonate, an alkylpolyglycoside, a naphthalenesulfonic acid formaldehyde condensate and a phosphate ester; and e) about 35% to about 50% water;

wherein all % are % by weight based upon the total weight of all components in the composition.

* * * * *